United States Patent [19]
Gorrell

[11] Patent Number: 6,078,182
[45] Date of Patent: Jun. 20, 2000

[54] RESISTANCE MEASURING METER WITH VOLTAGE MULTIPLIER

[75] Inventor: Brian Gorrell, Angola, Ind.

[73] Assignee: Illinois Tool Works Inc, Glenview, Ill.

[21] Appl. No.: 09/063,909

[22] Filed: Apr. 21, 1998

[51] Int. Cl.[7] ............................. G01R 27/08; G01R 11/63
[52] U.S. Cl. ...................... 324/713; 324/715; 324/103 R
[58] Field of Search .................... 324/713, 715,
324/717, 99 D, 115, 103 R; 361/235, 226,
284, 225

[56] References Cited

U.S. PATENT DOCUMENTS

| | | | |
|---|---|---|---|
| 4,200,814 | 4/1980 | Tanaka et al. | 324/117 H |
| 4,481,557 | 11/1984 | Woodruff | 361/235 |
| 5,446,374 | 8/1995 | Pradel | 324/142 |
| 5,735,958 | 4/1998 | Mauchle | 118/621 |

OTHER PUBLICATIONS

Harris Semiconductor, "ICL7136, ICL7137, 3½ LCD/LED, Low Power Display, A/D Converters with Overrange Recovery", Dec. 1997, pp. 1–17.
Harris Semiconductor, "Building a Battery Operated Auto ranging DVM With the ICL7106", pp. 3–118–3–122.
ITW Ransburg Electrostatic Systems, Test Assembly[SM], Model No. 70408–00 Operating Instructions manual, 1989, pp. 1–6.
ITW Ransburg Electrostatic Systems, Sprayability Meter[SM], Model No. 8333–00, Operating Instructions manual, Mar. 1987, pp. 1–4.
ITW Tansburg Electrostatic Systems, High Voltage Test Probe and Meter, Model 20791, Operating Instructions manual, Mar. 1986, pp. 1–6.

*Primary Examiner*—Josie Ballato
*Assistant Examiner*—Jermele M. Hollington

[57] ABSTRACT

An instrument for measuring the resistance of liquid paints and the surface resistance of articles to be coated electrostatically, includes a voltage multiplier circuit that multiplies a periodic low voltage signal to generate a resistance measuring voltage applied to first and second electrodes for resistance measurements. The electrodes are coupled to differential inputs of an A/D converter having an oscillator output for supplying the periodic low voltage signal to the multiplier circuit. Resistance, voltage and current measuring circuits are alternately switchable between the electrodes and the differential inputs of the A/D converter for measuring resistance, voltage and current, the results of which are displayed visually.

14 Claims, 9 Drawing Sheets

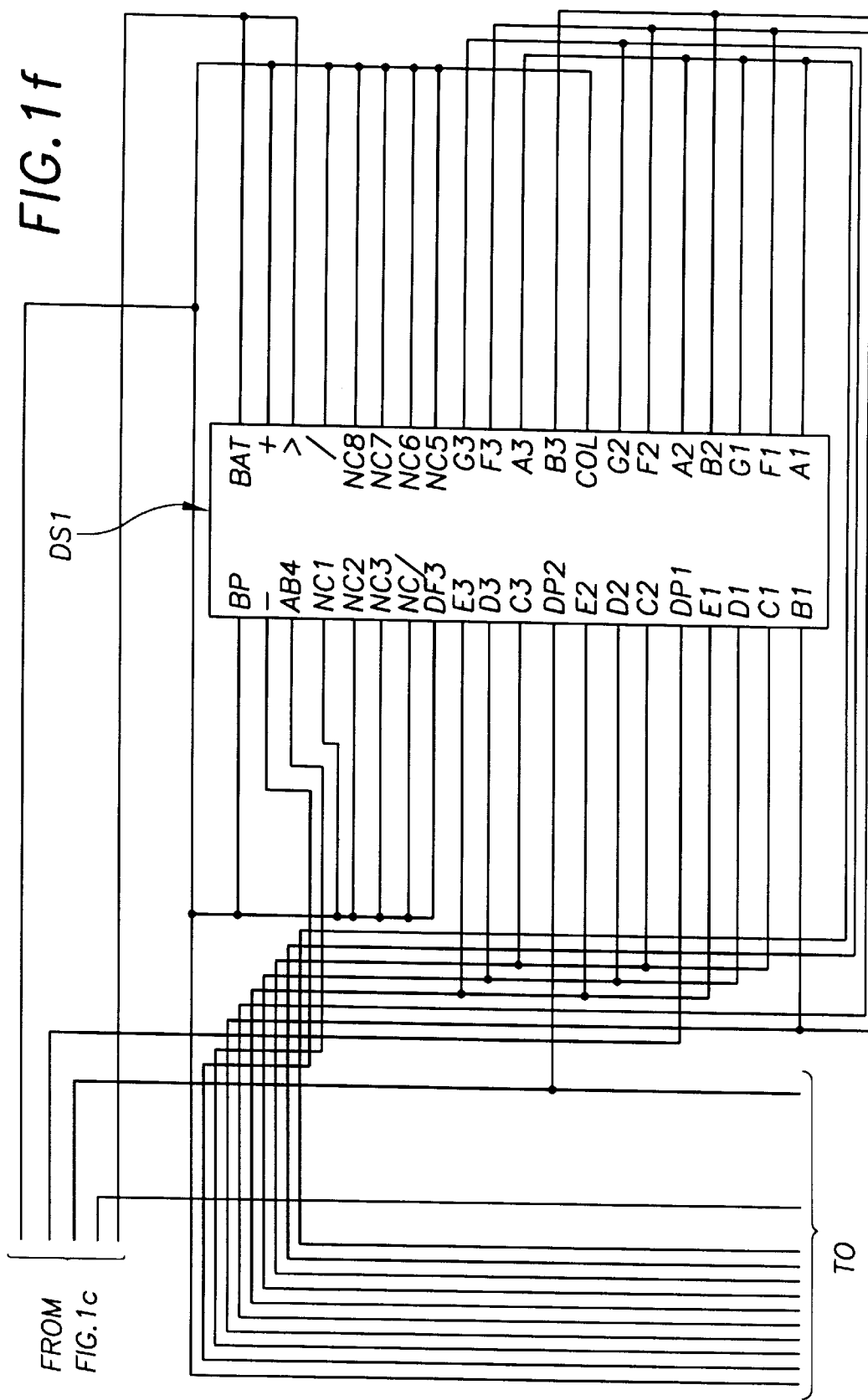

RESISTANCE MEASURING METER WITH VOLTAGE MULTIPLIER

BACKGROUND OF THE INVENTION

The invention relates generally to electrostatic coating operations, and more particularly to instruments for measuring electrical parameters, including the resistance of liquid paint formulations and the surface resistance of articles to be coated electrostatically.

In electrostatic coating operations, the electrical resistance of paint and articles coated therewith must be within specified ranges to ensure electrostatic efficiency. The resistance of the paint is relatively high, and ranges generally between approximately 0.05 megohms and approximately 1.0 megohms, more or less, depending on the particular electrostatic process employed. If paint resistance is outside the desired range, the paint will have a tendency to draw electrostatic charge from the high voltage electrode of the spray gun, adversely affecting electrostatic efficiency. The resistance of articles, and more particularly the surface resistances thereof, normally considered to be electrically non-conductive, must be sufficiently conductive to accept electrostatically charged coatings. The surface resistance of articles ranges generally between approximately 500 Kohms and approximately 1.5 Gohms, more or less, depending on the particular electrostatic process employed.

Instruments for measuring the resistance of liquid paint formulations and the surface resistance of articles for electrostatic coating applications are known generally, and are used to determine whether additives or treatments are necessary to alter the resistance, or conductivity, thereof. Solvents, for example, may be added to paints to decrease conductivity, and the surfaces of articles may be treated with preparations, for example Ransprep™, to increase conductivity. It is also desirable to measure resistance generally, including the resistance of other liquids and articles, for applications besides electrostatic coating operations.

One known instrument for measuring the electrical resistance of liquid paint formulations applied in electrostatic coating operations is the Test Assembly™, Model No. 70408-00, available from ITW Ransburg Electrostatic Systems, Angola, Ind. The Test Assembly™ includes generally a plug-in paint probe having concentrically arranged first and second electrodes with a relatively low voltage supplied by the meter applied therebetween. The probe is immersed into liquid paint, and current flowing through the paint between the electrodes forms a basis for measuring and displaying resistance on an ohmic scale of an analog meter. The Test Assembly™ also measures current, and more particularly the short circuit current of electrostatic spray guns. To measure this current, a high voltage from an external source is applied to the spray gun when leads of the Test Assembly™ are connected between a high voltage electrode of the spray gun and a ground point, whereby the measured current is displayed on an ampere scale of the analog meter.

One known instrument for measuring the electrical surface resistance of articles coated electrostatically is the Sprayability Meter™, Model No. 8333-00, also available from ITW Ransburg Electrostatic Systems, Angola, Ind. The Sprayability Meter™ includes generally two probes, or electrodes, protruding from the instrument with a relatively low voltage supplied by the meter applied therebetween. The electrodes are touched firmly against a surface of the article to be measured, and current flowing through the article and between the electrodes forms a basis for measuring and displaying the sprayability of the article on a proprietary measurement scale of an analog meter. Other known meters for measuring the surface resistance of articles apply relatively high voltages through electrodes thereto, but the high voltages pose a shock hazard to personnel, and are undesirable.

The Test Assembly™ and the Sprayability Meter™ both include a battery powered vacuum tube. The vacuum tubes however are relatively sensitive, and must be calibrated prior to nearly every measurement to compensate for temperature variations and decreasing battery power. The vacuum tubes are also very fragile and easily broken if the instruments are not handled carefully. Moreover, the availability of replacement tubes is declining, and the cost thereof is increasing.

The vacuum tubes also provide a limited range of linearity for measuring resistance and current. Measurements are therefore most accurate over a relatively small range. To compensate for the limited range of accuracy, the Test Assembly™ includes a resistance scale select switch. Measurements however are most accurate only near the center of each selected measurement scale, and the meter is susceptible to damage during switching between scales. Since the surface resistance of articles and the resistance of liquid paints applied thereto in electrostatic coating operations varies over a relatively wide range, and since vacuum tube operated meters are accurate for measurement purposes over relatively narrow ranges, separate instruments are required to perform these various resistance and current measurements.

In both the Test Assembly™ and the Sprayability Meter™ a single battery applies a relatively low 45 volts generally to the corresponding electrodes for resistance measurements. This voltage level is certified to ASTM and ISO industry standards and ensures accurate resistance measurements within the ranges characteristic of most paints and materials used in electrostatic coating operations. The commercial availability of replacement 45 volt batteries however is limited and the cost thereof is high. Additionally, the 45 volt batteries are only available in carbon, rather than alkaline, form and therefore have a relatively short life span. Also, if the meters remain switched in the calibrate mode, as often occurs, the resulting calibration current will dissipate battery power quickly. In the Test Assembly™, if a test probe with paint lodged between the electrodes thereof remains plugged into the instrument the resulting current through the paint will dissipate battery power. These tendencies to deplete battery power are aggravated by the lack of an on/off switch on the Test Assembly™ and on the Sprayability Meter™. The batteries must therefore be replaced frequently.

The present invention is drawn toward advancements in the art of electrical parameter measuring instruments useable for electrostatic coating operations.

It is an object of the invention to provide novel instruments and electrical circuits therefor for measuring resistance, especially the resistance of liquid paint formulations and the surface resistance of articles to be sprayed electrostatically, that are economical and that overcome problems in the prior art.

It is another object of the invention to provide novel resistance measuring instruments that operate efficiently on relatively low voltages supplied by standard, low cost and commercially available batteries, preferably a single 9 volt battery, the voltage of which is multiplied by a voltage multiplier circuit for applying a resistance measuring voltage between electrodes of the instrument.

It is a further object of the invention to provide novel resistance measuring instruments that comply with industry standards, particularly ASTM and ISO standards, applicable to measuring the resistance of liquid paint formulations and the surface resistance of articles to be coated electrostatically.

Another object of the invention is to provide novel electrical parameter measuring instruments that are accurate over relatively broad measurement ranges including resistance, voltage and current measurement ranges, and are thus suitable for measuring the surface resistance and resistance of liquid paints with a single meter.

It is a more particular object of the invention to provide novel resistance measuring instruments, useable for electrostatic coating applications, comprising generally first and second electrodes with a resistance measuring voltage applied therebetween, the resistance measuring voltage is generated by a voltage multiplier circuit having a first capacitor coupled to a first diode cathode and to a second diode anode, a second capacitor coupled to the second diode cathode and to an output diode anode, a first inverter coupled to the second capacitor. A periodic low voltage signal applied to the second capacitor is inverted relative to the same periodic low voltage signal applied to the first capacitor, whereby the periodic low voltage signal is multiplied to generate the resistance measuring voltage. Additional, similarly configured voltage multiplier stages multiply the periodic low voltage signal further.

It is another more particular object of the invention to provide novel resistance measuring instruments, useable for electrostatic coating applications, further comprising generally an A/D converter having differential inputs coupled to the first and second electrodes through a divider network, the A/D converter including an oscillator output for supplying the periodic low voltage signal to the multiplier circuit.

It is yet another more particular object of the invention to provide novel resistance measuring instruments, useable for electrostatic coating applications, further comprising a voltage measuring circuit switchable between the first and second electrodes and the differential inputs of the A/D converter for measuring voltages applied to the first and second electrodes, and a current measuring circuit switchable between the first and second electrodes and the differential inputs of the A/D converter for measuring currents applied to the first and second electrodes.

It is still another more particular object of the invention to provide novel electrical parameter measuring instruments, useable for electrostatic coating applications, further comprising a display coupled to and driven by the A/D converter, whereby resistance, voltage and current measurement results based on input signals to the differential inputs of the A/D converter are displayed visually.

These and other objects, aspects, features and advantages of the present invention will become more fully apparent upon careful consideration of the following Detailed Description of the Invention and the accompanying Drawings, which may be disproportionate for ease of understanding, wherein like structure and steps are referenced generally by corresponding numerals and indicators.

BRIEF DESCRIPTION OF THE DRAWINGS

FIG. 1f is another partial electrical schematic of the electrical parameter measuring instrument.

DETAILED DESCRIPTION OF THE INVENTION

FIGS. 1a–1h illustrate an electrical schematic of an instrument useable for measuring various electrical parameters, particularly the resistance of liquid paint formulations used in electrostatic coating applications and the surface resistance of articles coated electrostatically. The instrument comprises generally first and second electrodes A and B, and circuitry coupled to a digital A/D converter circuit U3 for measuring voltage, current and resistance, and displaying measured results on a display DS1.

Figure 1:
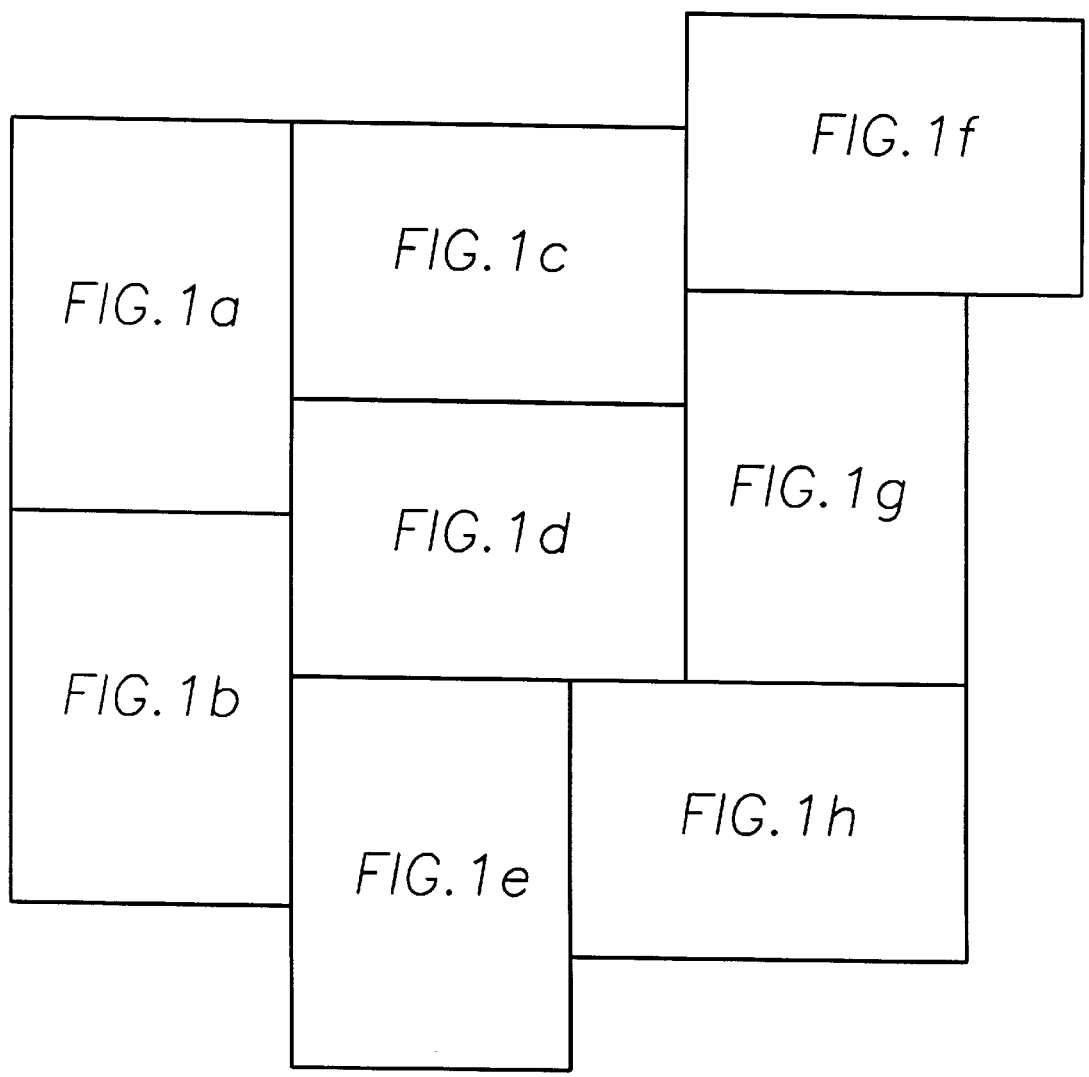
FIG. 1 is an overview of several drawing sheets illustrating electrical schematic of an electrical parameter measuring instrument useable for measuring resistance of liquid paint formulations and articles to be coated electrostatically.
Figure 1A:
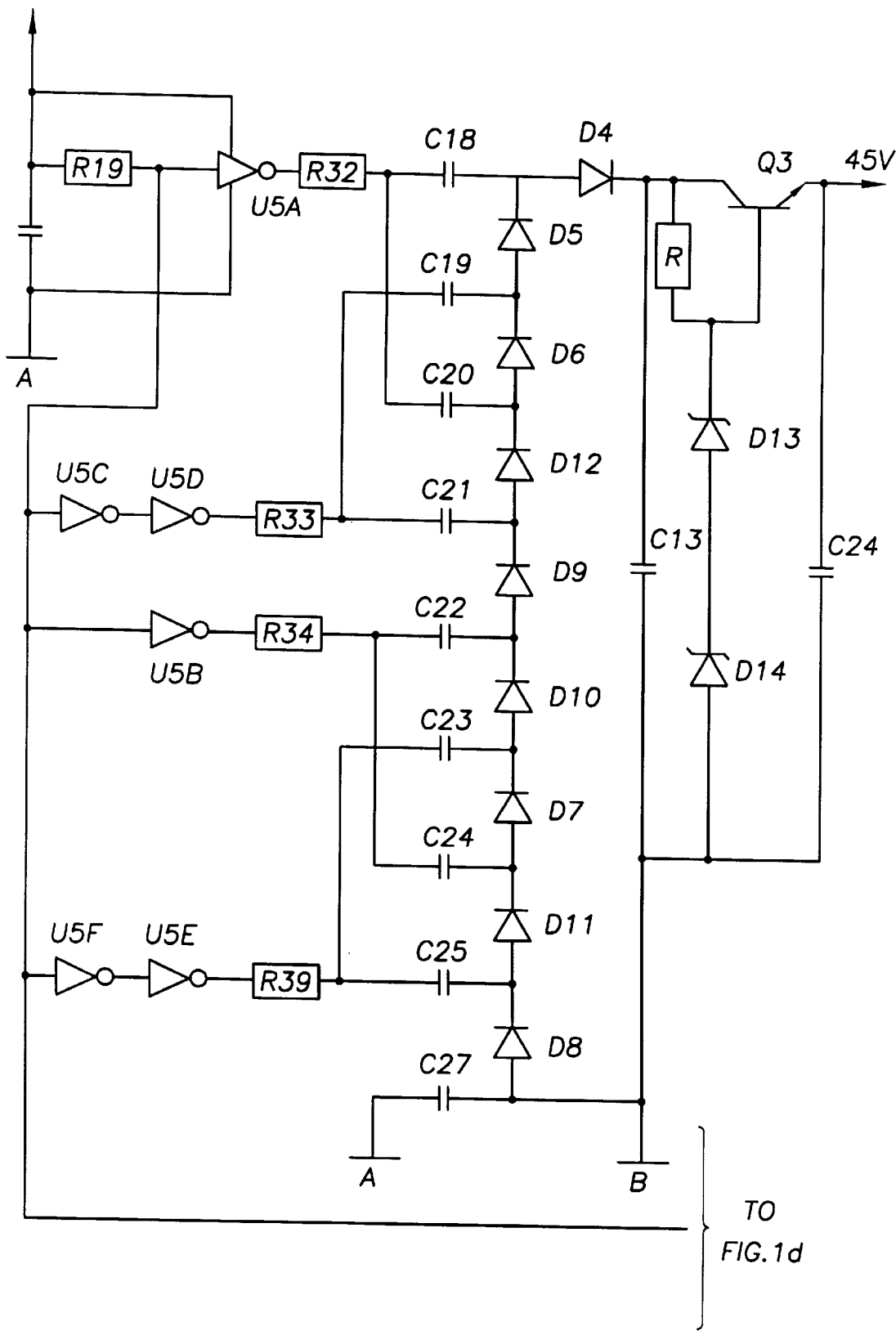
FIG. 1a is a partial electrical schematic of the electrical parameter measuring instrument.
Figure 1B:
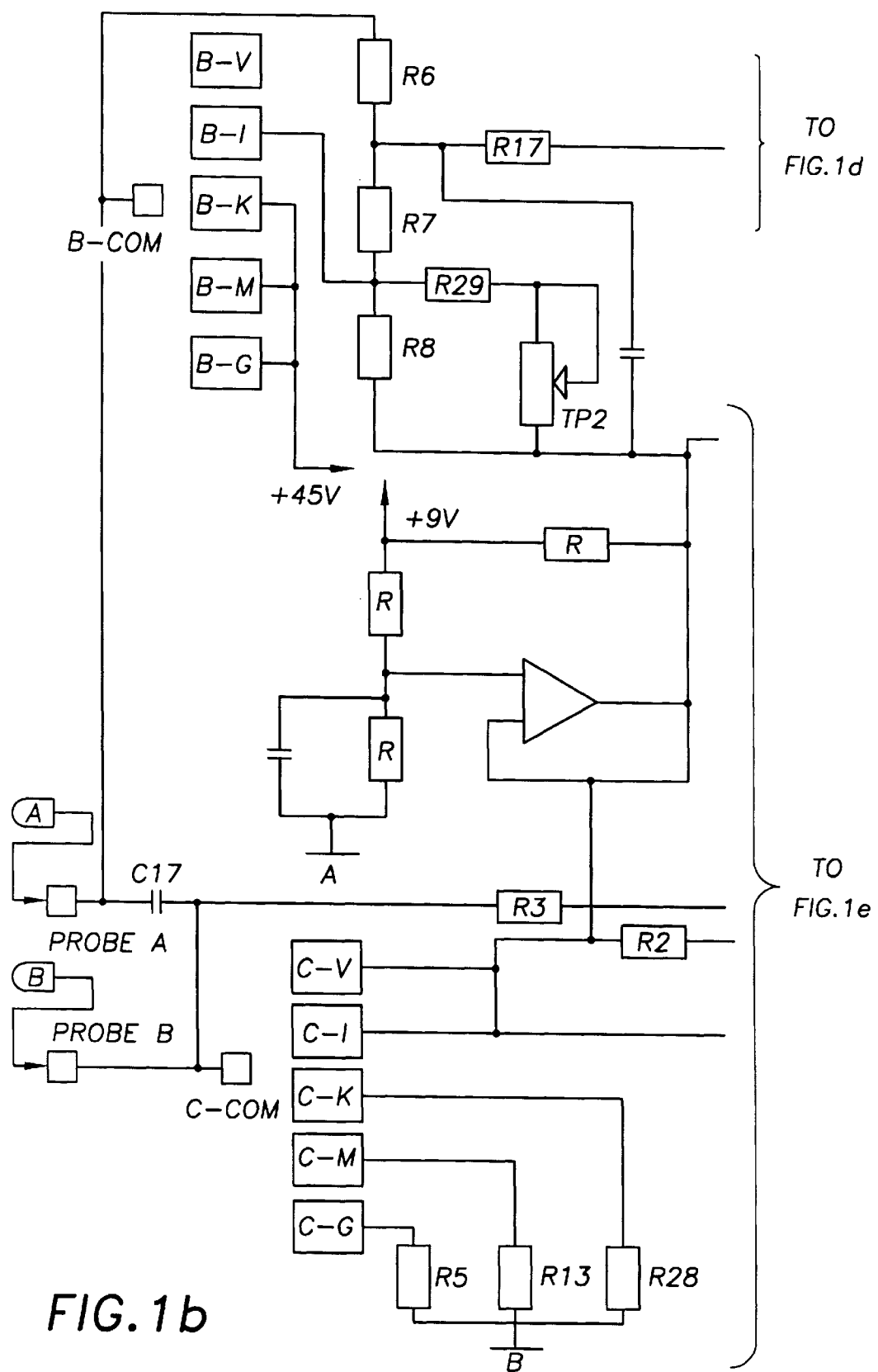
FIG. 1b is another partial electrical schematic of the electrical parameter measuring instrument.
Figure 1C:
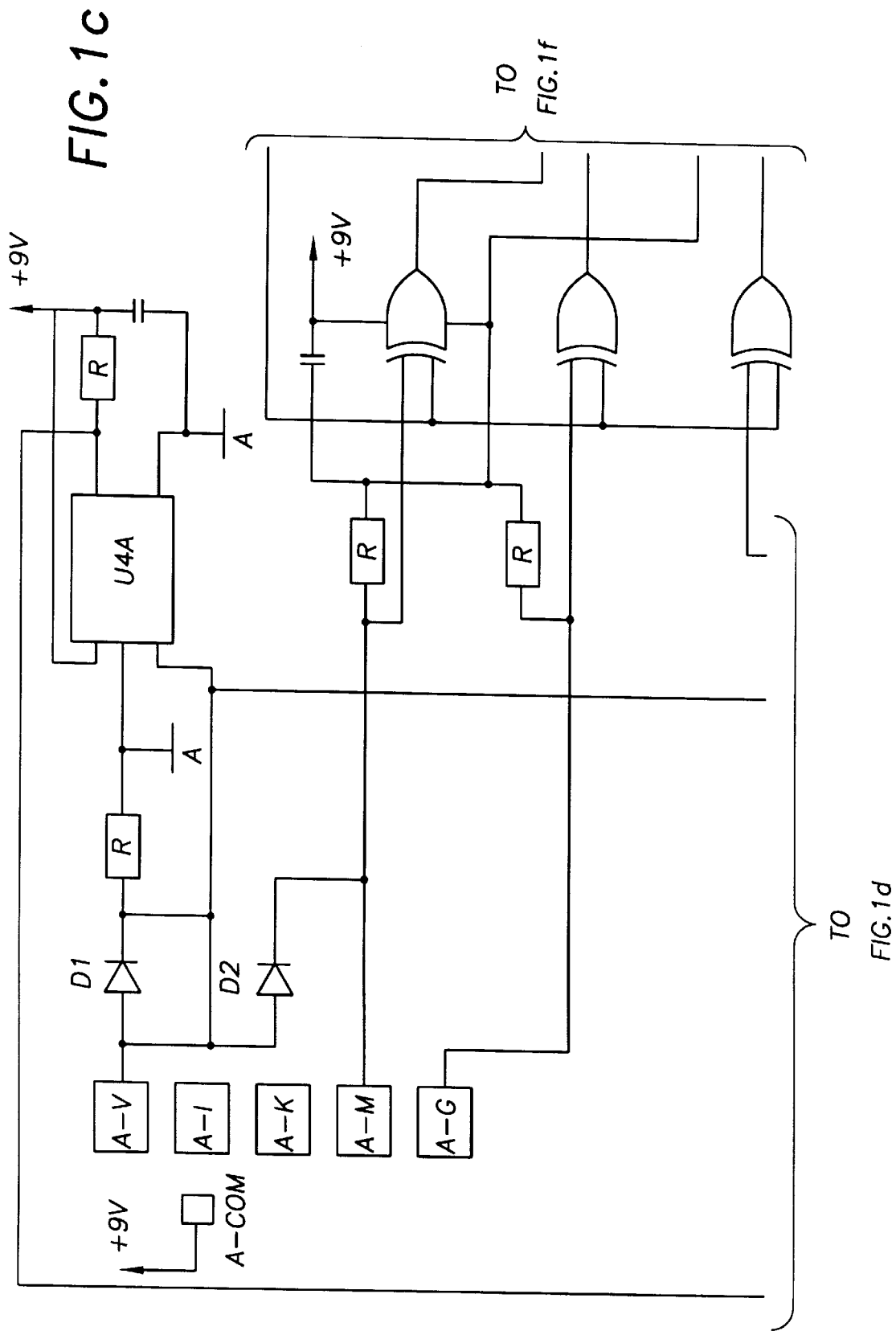
FIG. 1c is another partial electrical schematic of the electrical parameter measuring instrument.
Figure 1D:
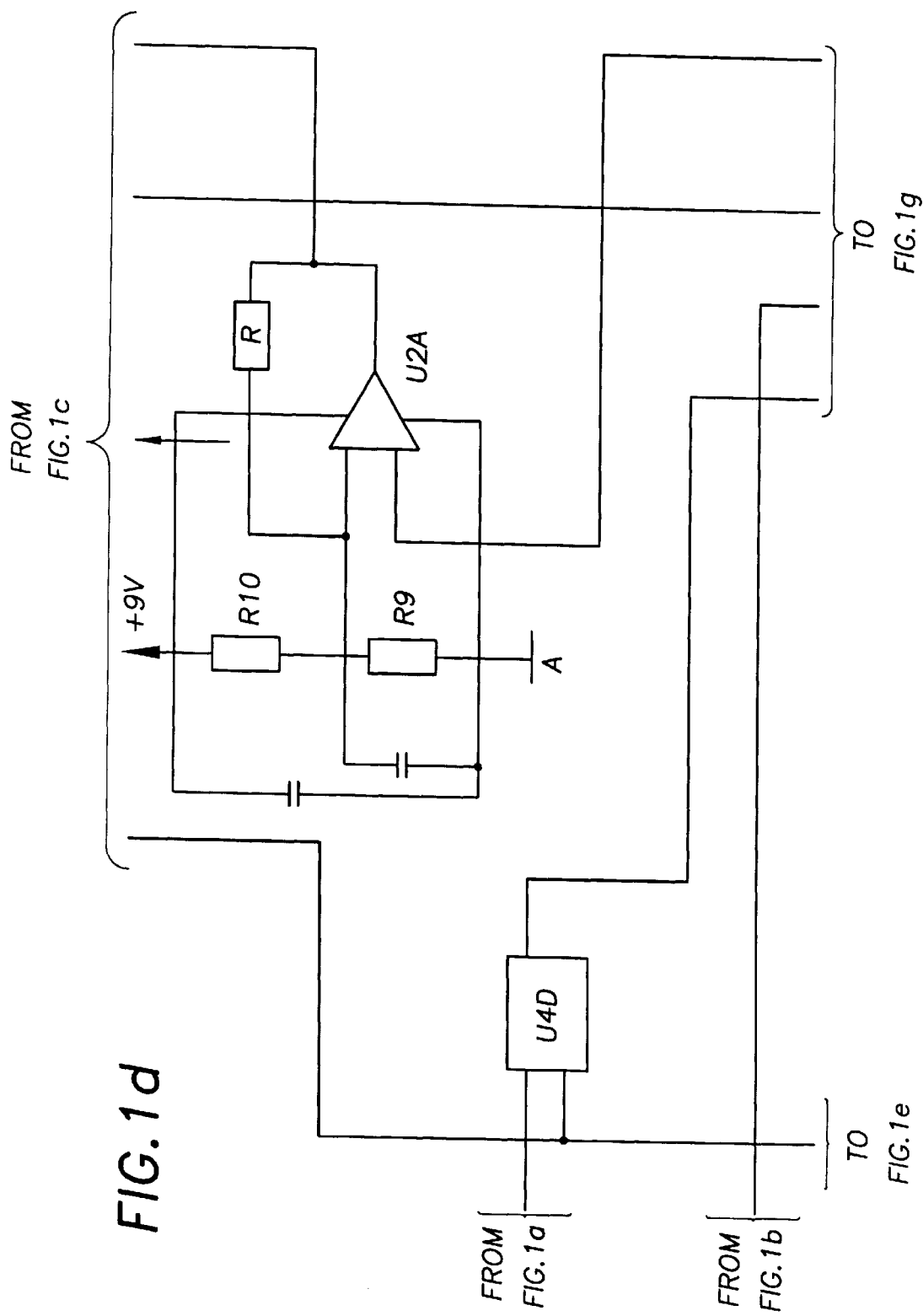
FIG. 1d is another partial electrical schematic of the electrical parameter measuring instrument.
Figure 1E:
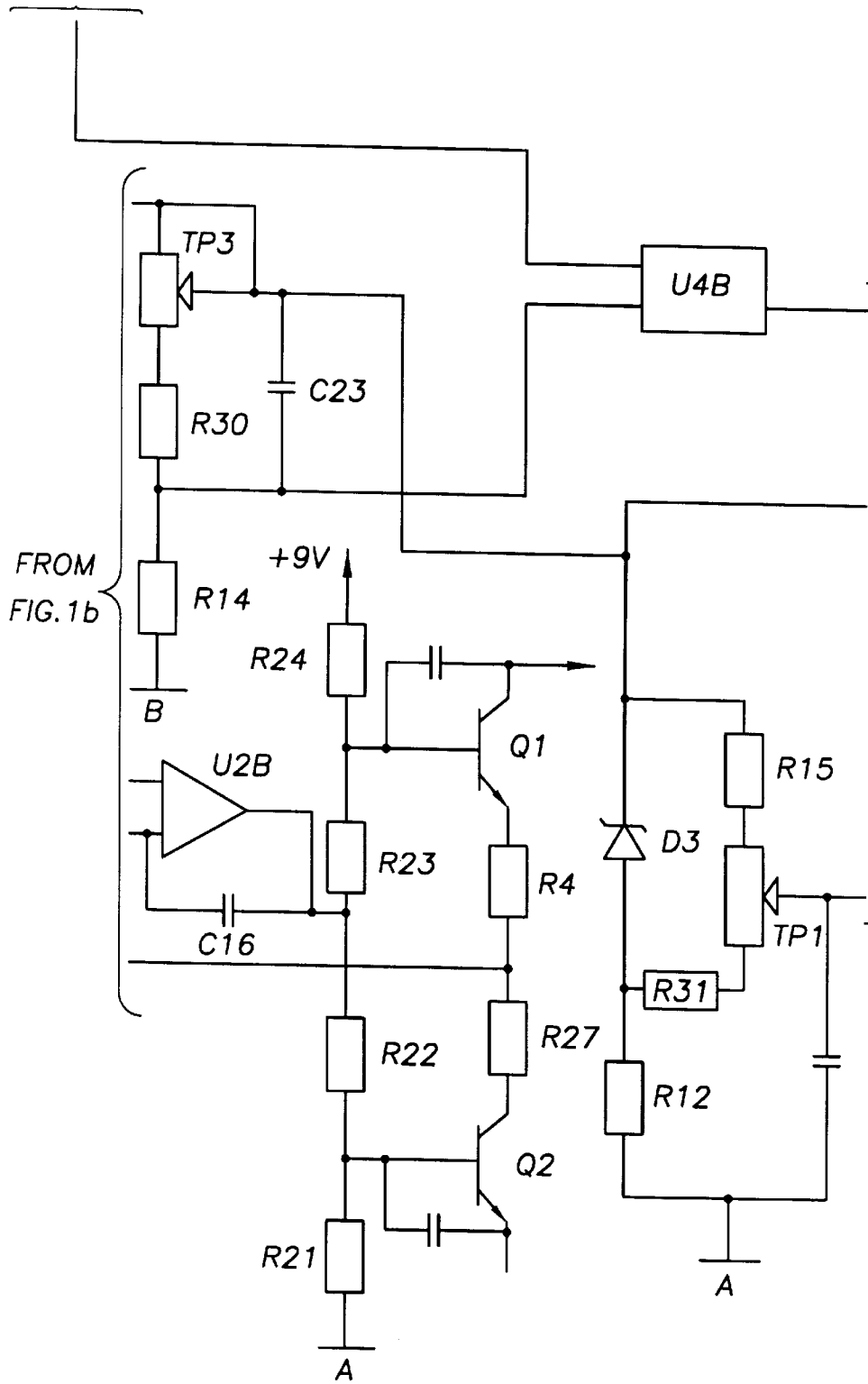
FIG. 1e is another partial electrical schematic of the electrical parameter measuring instrument.
Figure 1G:
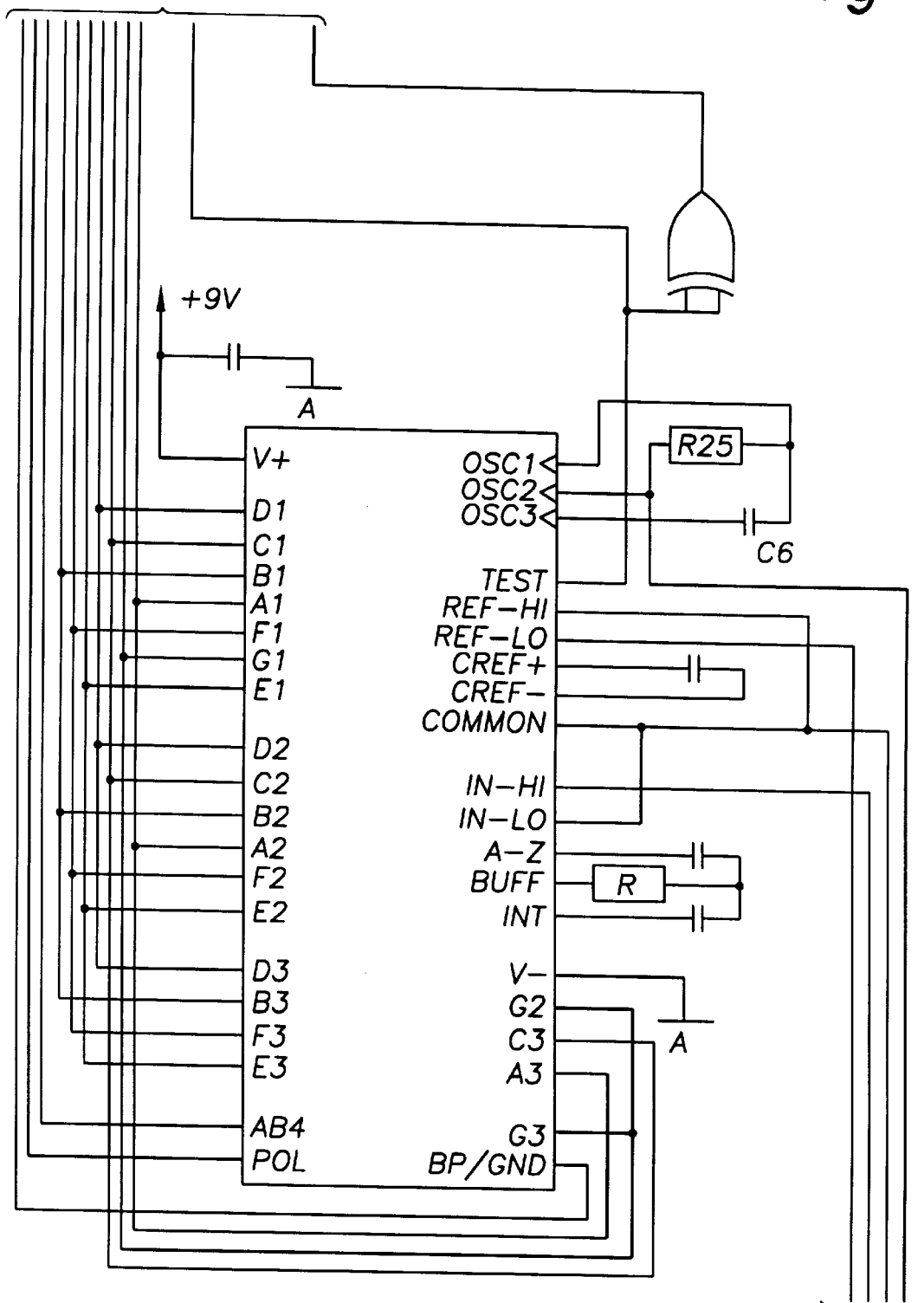
FIG. 1g is another partial electrical schematic of the electrical parameter measuring instrument.
Figure 1H:
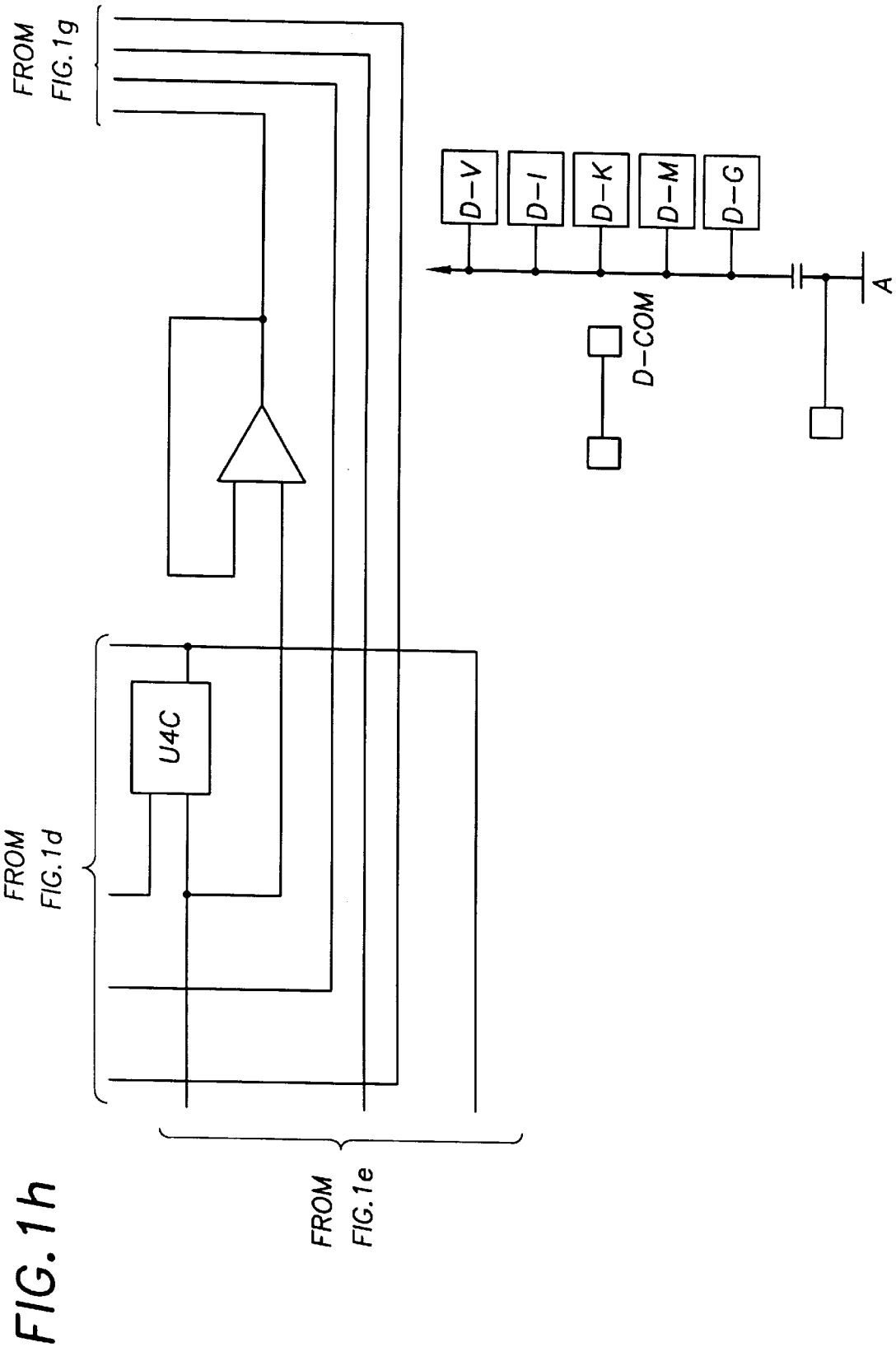
FIG. 1h is another partial electrical schematic of the electrical parameter measuring instrument.

In FIGS. 1f and 1g, the digital A/D converter circuit U3 in the exemplary embodiment is a Harris ICL7136 low power A/D converter, which drives an LCD display DS1, for example, Varitronix 3½ digit LCD, Part No. VI-39-DPRCS. The Harris ICL7136 A/D converter circuit U3 is configurable as a 9 volt battery powered digital multi-meter for measuring voltage, resistance and current as described generally in Harris Semiconductor publication entitled "ICL7136, ICL7137, 3½ Digit LCD/LED, Low Power Display, A/D Converters with Overrange Recovery", and Harris Semiconductor publication entitled "Building a Battery Operated Auto Ranging DVM With the ICL7106". Other digital A/D converter circuits, or alternatively analog circuits, may be used generally for this purpose.

The electrodes A and B may take many forms, and are preferably removably connectable to corresponding plug-in probe A and B connector jacks on the instrument. The electrodes A and B may be first and second concentrically arranged electrodes of a paint probe coupleable to the plug-in probe A and B connector jacks for measuring the resistance of liquid paint formulations of the type used in the Test Assembly™, Model No. 70408-00, available from ITW Ransburg Electrostatic Systems, Angola, Ind. Alternatively, the electrodes A and B may be of the type for measuring the surface resistance of articles to be coated electrostatically as used in the Sprayability Meter™, Model No. 8333-00, also available from ITW Ransburg Electrostatic Systems, Angola, Ind. Other electrode configurations and types are useable alternatively.

FIG. 1a illustrates a voltage multiplier circuit for multiplying a relatively low voltage, 9 volts supplied by a battery in the exemplary embodiment, for application to the first and second electrodes A and B during resistance measurements. The voltage multiplier is driven by a periodic low voltage signal produced by an oscillator circuit or some other source and applied generally to a parallel arrangement of inverting buffers U5A, U5C, U5B and U5F, for example Motorola Part No. MC14049BCP, coupled to the voltage multiplier stages as discussed further below.

The voltage multiplier circuit comprises generally a first multiplier stage including a first capacitor C25 coupled to a first diode D8 cathode and to a second diode D11 anode. A second capacitor C24 is coupled to the second diode D11 cathode. In the exemplary embodiment, the second diode D11 is coupled to one or more additional multiplier stages, as discussed further below. In embodiments where less than all of the exemplary multiplier stages is desired, however, the second diode D11 cathode is coupled directly to an output diode D4 anode. The periodic low voltage signal is applied to the first and second capacitors C25 and C24 in parallel, and a first inverter U5B is coupled in series to the second capacitor C24. The periodic low voltage signal applied to the second capacitor C24 is thus inverted relative to the periodic low voltage signal applied to the first capacitor C25, whereby the periodic low voltage signal applied to the first and second capacitors C25 and C24 is 180 degrees out of phase. The first and second electrodes A and B are connectable to a relatively high voltage output of the voltage multiplier circuit taken between the first diode D8 anode and the output diode D4 cathode as discussed further below. The voltage multiplier circuit of the present invention is not as current limited as known cascade voltage multiplier circuits.

In the exemplary embodiment, the periodic low voltage signal is provided by an oscillator output OSC2 of the digital A/D converter circuit U3 to a bi-directional analog switch U4D, for example Motorola, Part No. MC140BCP, coupled in series between the oscillator circuit output and the voltage multiplier. Other oscillator circuits may be used alternatively. The periodic low voltage signal supplied to the first capacitor C25 is preferably inverted twice by a serial arrangement of inverters U5F and U5E. The current supplied to the first and second capacitors C25 and C24 is also preferably limited by corresponding 200 ohm resistors R39 and R34 coupled in series with the corresponding inverters U5E and U5B, respectively.

In FIG. 1g the periodic low voltage signal has an oscillation frequency and duty cycle generally within the oscillation frequency and duty cycle ranges of the digital A/D converter, when supplied thereby. The oscillation frequency of the Harris ICL7136A/D converter circuit U3 is controlled by resistor R25 and capacitor C6. In one embodiment, resistor R25 is 560 Kohm and capacitor C6 is 50 pF, whereby the periodic low voltage signal has a frequency of approximately 16 KHz. The periodic low voltage signal is a generally rectangular wave having a duty cycle between approximately 30 percent and approximately 50 percent. In the exemplary embodiment, the periodic low voltage signal is offset positively by a DC bias voltage supplied for example by a 9 volt battery across a 200 Kohm resistor R19 illustrated in FIG. 1a.

Additional multiplier stages further multiply the voltage at the output of the voltage multiplier circuit. FIG. 1a illustrates, more particularly, a third capacitor C23 coupled to a third diode D7 cathode and to a fourth diode D10 anode, wherein the second capacitor C24 and the second diode D11 cathode are coupled to the third diode D7 anode. A fourth capacitor C22 is coupled to the fourth diode D10 cathode. In the exemplary embodiment, the fourth diode D10 is coupled to additional multiplier stages, as discussed further below. In embodiments where fewer than all of the exemplary multiplier stages is desired, however, the fourth diode D10 cathode is coupled directly to the output diode D4 anode. The periodic low voltage signal is applied generally to the third and fourth capacitors C23 and C22 in parallel with each other and in parallel with the first and second capacitors C25 and C24.

The first inverter U5B is coupled in series to the second and fourth capacitors C24 and C22. The periodic low voltage signal applied to the second and fourth capacitors C24 and C22 is thus inverted, 180 degrees out of phase, relative to the periodic low voltage signal applied to the first and third capacitors C25 and C23. The periodic low voltage signal applied to the third capacitor C23 is also preferably inverted twice by the serial arrangement of inverters U5F and U5E. The current supplied to the third and fourth capacitors C23 and C22 is also preferably limited by the corresponding 200 ohm resistors R39 and R34 coupled in series with inverters U5E and U5B, respectively, as discussed above.

FIG. 1a also illustrates additional voltage multiplier stages stacked on the multiplier stages discussed above. A fifth capacitor C21 is coupled to a fifth diode D9 cathode and to a sixth diode D12 anode, wherein the fourth capacitor C22 and the fourth diode D10 cathode are coupled to the fifth diode D9 anode. A sixth capacitor C20 is coupled to the sixth diode D12 cathode, wherein the fifth capacitor C21 and the fifth diode D9 cathode are coupled to the sixth diode D12 anode. A seventh capacitor C19 is coupled to a seventh diode D6 cathode, wherein the sixth capacitor C20 and the sixth diode D12 cathode are coupled to the seventh diode D6 anode. An eighth capacitor C18 is coupled to an eighth diode D5 cathode and to the output diode D4 anode, wherein the seventh capacitor C19 and the seventh diode D6 cathode are coupled to the eighth diode D5 anode.

The periodic low voltage signal is applied generally to the fifth, sixth, seventh and eighth capacitors C21, C20, C19 and C18 in parallel with each other and in parallel with the first, second, third and fourth capacitors C25, C24, C23 and C22. A fourth inverter U5A is coupled in series to the sixth and eight capacitors C20 and C18, wherein the periodic low voltage signal applied to the first, third, fifth and seventh capacitors C25, C23, C21 and C19 is inverted relative to the periodic low voltage signal applied to the second, fourth, sixth and eighth capacitors C24, C22, C20 and C18. The periodic low voltage signal applied to the fifth and seventh capacitors C21 and C19 is preferably twice inverted by the serial arrangement of inverters U5C and U5D. The current supplied to the fifth and seventh capacitors C21 and C19 and to the sixth and eight capacitors C20 and C18 is also preferably limited by corresponding 200 ohm resistors R33 and R32 coupled in series with inverters U5D and U5A, respectively.

The exemplary voltage multiplier circuit multiplies approximately 9 volts to between approximately 65 and approximately 70 volt at a high voltage output thereof between the first diode D8 anode and the output diode D4 cathode. In the exemplary embodiment, the value of the capacitors comprising the voltage multiplier circuit including capacitors C13 and C27 are 0.1 $\mu$F rated at 100 V, and the diodes thereof are 1N914 devices.

In FIG. 1a, a voltage regulator circuit is preferably coupled across the high voltage output of the voltage multiplier circuit between the first diode D8 anode and the output diode D4 cathode. The voltage regulator circuit comprises generally an NPN transistor Q3 rated at 50 V, for example a 2N3417 device, with a serial arrangement of zener diodes D13 and D14 each rated at 22 V, for example IN5251 devices, coupled to the base thereof. A 0.1 $\mu$F filtering capacitor C24 rated at 100 V is coupled between the emitter of the transistor Q3 and the anode of the first diode D8. The voltage regulator circuit provides approximately 45 VDC across capacitor C24 available for application to the electrodes A and B during resistance measurements, as discussed further below. Other voltage regulator circuits may be used alternatively.

In FIG. 1b, for resistance measuring operations, the instrument generally applies a resistance measuring voltage, based on the approximately 45 VDC output of the voltage multiplier circuit, to electrodes A and B through a switch. More particularly, the 45 VDC output from the voltage multiplier circuit is applied to the electrode A through any one of three resistance range measuring positions B-K, B-M and B-G selected by rotating a commutator B-com of a multi-position switch. The 45 VDC is applied also to a differential input of the A/D converter U3, which in the exemplary embodiment is the IN-HI input pin 31, through a divider network including a 100 Mohm resistor R6 and a 100 Mohm resistor R17.

The electrode B is coupled to a commutator C-com of the multi-position switch, which selectively couples the electrode B to any one of three corresponding resistance measurement scaling resistors including a 1 Gohm resistor R5, a 10 Mohm resistor R13, and a 100 Kohm resistor R28. In FIGS. 1a and 1b, resistance measurement scaling resistors R5, R13 and R28 are coupled to the first diode D8 anode, and to another differential input of the A/D converter U3, which in the exemplary embodiment is the IN-LO input, through a divider network including 1 Mohm resistor R14, a 100 Kohm resistor R30, and a 20 Kohm calibration potentiometer TP3.

A resistance measurement signal supplied from the electrodes A and B, contacting the test subject, to the differential inputs of the A/D converter U3 forms the basis for resistance measurements by the instrument, wherein the A/D converter U3 displays resistance measurement results on the display DP1 as discussed above. The instrument accurately measures resistance over a relatively wide range from zero up to approximately 900 Gohms, and is thus particularly suitable for measuring resistances over the ranges typical of electrostatic applications, including surface resistances of articles sprayable electrostatically and resistances of liquid paint formulations.

FIGS. 1b, 1d, 1e, and 1g illustrate, for voltage measuring operations, the electrode A is isolated from the 45 VDC output of the voltage multiplier circuit by positioning the B-com commutator of the multi-position switch to the B-V position. The electrode A is however coupled to the IN-HI differential input of the A/D converter U3 through the divider network including a 100 Mohm resistor R6 and a 100 Mohm resistor R17. The electrode B is coupled to the IN-LO differential input of the A/D converter U3 by positioning commutator C-com to the C-V position. A voltage measurement signal supplied from the electrodes A and B contacting the test subject to the differential inputs of the A/D converter U3 forms the basis for voltage measurements by the instrument, wherein the A/D converter U3 displays voltage measurement results on the display DP1 as discussed above. The instrument accurately measures voltage over a relatively wide range from zero up to approximately 199 KV.

FIGS. 1b, 1d, 1e, and 1g illustrate, for current measuring operations, the electrode A is isolated from the 45 VDC by positioning the B-com commutator of the multi-position switch to the B-I position. The electrode A is however coupled to the IN-HI differential input of the A/D converter U3 through the divider network including the 100 Mohm resistor R6, and the 100 Mohm resistor R17. The B-com commutator also couples the electrode A to a current calibration circuit including a 1.0 Mohm resistor R7, a 1.05 Mohm resistor R8, a 15 Kohm resistor R29, and a 20 Kohm potentiometer TP2. The electrode B is coupled to the IN-LO differential input of the A/D converter U3 by positioning commutator C-com to the C-I position. A current measurement signal supplied from the electrodes A and B contacting the test subject to the differential inputs of the A/D converter U3 forms the basis for current measurements by the instrument, wherein the A/D converter U3 displays current measurement results on the visual display DP1 as discussed above. The instrument accurately measures current over a relatively wide range from zero up to approximately 999 $\mu$A.

The multi-position switch illustrated in the drawing includes four poles A-com, B-com, C-com and D-com on a common commutator switchable through through 5 positions for selectively measuring resistance, voltage and current as discussed above, and includes preferably an OFF position not shown in the drawing. The multi-position switch is preferably a commutating switch, for example a Grayhill, four pole, six position switch, Part No. 71BD30-02-2-06N.

FIGS. 1b, 1e, and 1g illustrate in both the voltage and current measuring configurations, the electrode A is coupled also to a precision op-amp U2B input, for example a Texas Instruments, TLC27L9NC device, by an isolation 1000 pF capacitor C17 rated at 1000 volts, and a 100 Mohm current limiting resistor R3 when the commutator B-com is positioned in the B-V position. The electrode B is also coupled to the op-amp U2B by a 100 Mohm resistor R2 when the commutator C-com is positioned in the C-V position. The op-amp U2B drives complementary transistors Q1 and Q2, for example 2N3417 and 2N5086 devices respectively, which are biased by 9 and 45 VDC and 820 Kohm resistors R21 and R24, 150 Kohm resistors R22 and R23, a 5.1 Kohm resistor R4, and a 1.0 Mohm resistor R7. The op-amp U2B is driven by inputs from the electrode A and B and a feedback signal from the emitters of the Q1 and Q2, which also biases the IN-LO differential input of the A/D converter U3. A 0.01 $\mu$F feedback capacitor C16 suppresses oscillation of the op-amp U2B.

In FIG. 1e, the instrument includes an internal voltage reference and calibration circuit comprising generally a precision reference 1.2 volt zener diode D3, for example a LM385BZ device, clamping a 330 Kohm resistor R15, a 20 Kohm potentiometer TP1, and a 78.7 Kohm resistor R31, which are in series with a 51 Kohm resistor R12. The voltage reference circuit provides a reference voltage to a comparator circuit comprising a precision op-amp U2A, for example the Texas Instruments, TLC27L9NC device. The battery supplied 9 VDC is divided by a 110 Kohm resistor R9 and a 200 Kohm resistor R10 and input to the op-amp U2A, which may disable the instrument or display or both when the battery supply becomes depleted below a specified level.

The instrument of the present invention operates on relatively low current, and is powered by batteries, which have a relatively long life span and are inexpensive to replace. The instrument is preferably comprised generally of solid state components and integrated circuits, for example the A/D converter circuit U3, and therefore does not require repeated calibration to compensate for temperature variations and reductions in available battery power as do the vacuum tube operated instruments of the prior art. The instrument is also relatively mechanically and electrically robust, lightweight and is produced economically. In addition to measuring resistance over relatively wide measurement ranges, the instrument is also configurable for selectively measuring voltage and current over correspondingly relatively wide measurement ranges, which increases the general utility thereof.

While the foregoing written description of the invention enables one of ordinary skill in the art to make and use what is at present considered to be the best mode of the invention, those of ordinary skill in the art will appreciate and understand the existence of variations, combinations, modifications and equivalents of the specific exemplary embodiments disclosed herein. The present invention is therefore to be limited not by the specific exemplary embodiments disclosed herein but by all embodiments within the spirit and scope of the appended claims.

What is claimed is:

1. An instrument for measuring resistance in electrostatic coating applications, the instrument comprising:

first and second electrodes;

a voltage multiplier circuit having a first capacitor coupled to a first diode cathode and to a second diode anode, a second capacitor coupled to a second diode cathode and to an output diode anode, a periodic low voltage signal applied to the first capacitor and to the second capacitor in parallel;

a first inverter coupled in series with the second capacitor, the periodic low voltage signal applied to the second capacitor inverted relative to the periodic low voltage signal applied to the first capacitor, the periodic low voltage signal multiplied by the voltage multiplier circuit at a high voltage output between a first diode anode and an output diode cathode, the high voltage output of the voltage multiplier circuit coupled to the first and second electrodes to apply a resistance measuring voltage to the first and second electrodes.

2. The instrument of claim 1 further comprising a third capacitor coupled to a third diode cathode and to a fourth diode anode, the second capacitor and the second diode cathode coupled to a third diode anode, and a fourth capacitor coupled to a fourth diode cathode and to the output diode anode, the first inverter coupled in series to the fourth capacitor, the periodic low voltage signal applied to the second and fourth capacitors inverted relative to the periodic low voltage signal applied to the first and third capacitors.

3. The instrument of claim 1 further comprising second and third inverters coupled in series to the first capacitor.

4. The instrument of claim 2 further comprising:

a fifth capacitor coupled to a fifth diode cathode and to a sixth diode anode, the fourth capacitor and the fourth diode cathode coupled to a fifth diode anode;

a sixth capacitor coupled to a sixth diode cathode, the fifth capacitor and the fifth diode cathode coupled to a sixth diode anode;

a seventh capacitor coupled to a seventh diode cathode, the sixth capacitor and the sixth diode cathode coupled to a seventh diode anode;

an eighth capacitor coupled to an eighth diode cathode and to the output diode anode, the seventh capacitor and the seventh diode cathode coupled to an eighth diode anode;

a fourth inverter coupled in series to the sixth and eight capacitors, the periodic low voltage signal applied to the first, third, fifth and seventh capacitors inverted relative to the periodic low voltage signal applied to the second, fourth, sixth and eighth capacitors.

5. The instrument of claim 4 further comprising second and third inverters coupled in series to the first and third capacitors, and fifth and sixth inverters coupled in series to the fifth and seventh capacitors.

6. The instrument of claim 1 further comprising a filtering capacitor and a voltage regulator circuit coupled in parallel across the high voltage output of the voltage multiplier between the first diode anode and the output diode cathode.

7. The instrument of claim 1 further comprising an oscillator circuit having an oscillator output producing the periodic low voltage signal, the periodic low voltage signal has a frequency of approximately 15 KHz and a duty cycle between approximately 30 percent and approximately 50 percent.

8. The instrument of claim 7, the periodic low voltage signal from the oscillator output biased positively by a DC voltage.

9. The instrument of claim 1, the first and second electrodes are at least partially concentric electrodes, the resistance measuring voltage applied to the first and second electrodes is useable for measuring resistance of liquid paint formulations and surface resistance of articles to be coated electrostatically.

10. The instrument of claim 1 further comprising an A/D converter having differential inputs coupled to the first and second electrodes through a divider network, the A/D converter including an oscillator output for supplying the periodic low voltage signal, and a bidirectional analog switch coupled in series between the oscillator output of the A/D converter and the first and second capacitors.

11. The instrument of claim 10 further comprising a display device coupled to and driven by the A/D converter, whereby the display device displays resistance measurement results based on an input signal to the differential inputs of the A/D converter.

12. The instrument of claim 10 further comprising a voltage measuring circuit switchable between the first and second electrodes and the differential inputs of the A/D converter for measuring voltage applied to the first and second electrodes.

13. The instrument of claim 10 further comprising a current measuring circuit switchable between the first and second electrodes and the differential inputs of the A/D converter for measuring current applied to the first and second electrodes.

14. The instrument of claim 1 further comprising a multi-position switch coupling one of the first and second electrodes to one of a plurality of corresponding resistance measurement scaling resistors.

* * * * *